(12) United States Patent
Tsuchiya et al.

(10) Patent No.: US 7,745,354 B2
(45) Date of Patent: Jun. 29, 2010

(54) CLEANING TOOL

(75) Inventors: Akemi Tsuchiya, Kagawa (JP); Masatoshi Fujiwara, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 604 days.

(21) Appl. No.: 11/300,268

(22) Filed: Dec. 15, 2005

(65) Prior Publication Data

US 2006/0137116 A1   Jun. 29, 2006

(30) Foreign Application Priority Data

Dec. 28, 2004   (JP)   ............... 2004-381391

(51) Int. Cl.
   *A47L 13/40*   (2006.01)
   *B32B 27/12*   (2006.01)
(52) U.S. Cl. .................. 442/123; 442/381; 442/392; 442/411; 442/415; 15/1.52; 15/226; 15/229.4
(58) Field of Classification Search ................. None
   See application file for complete search history.

(56) References Cited

U.S. PATENT DOCUMENTS

| | | | |
|---|---|---|---|
| 4,806,526 A | | 2/1989 | Green |
| 4,874,659 A | * | 10/1989 | Ando et al. .............. 428/221 |
| 4,977,142 A | | 12/1990 | Green |
| 6,494,921 B1 | * | 12/2002 | Bennett .................... 8/142 |
| 2002/0040055 A1 | * | 4/2002 | Inui et al. ................. 514/492 |
| 2002/0100494 A1 | * | 8/2002 | Brown et al. .............. 134/6 |
| 2004/0007251 A1 | | 1/2004 | Koenig et al. |
| 2004/0254245 A1 | * | 12/2004 | Lintner ..................... 514/560 |
| 2005/0000050 A1 | * | 1/2005 | Galvin et al. .............. 15/226 |
| 2005/0220911 A1 | * | 10/2005 | Shigemura ................ 424/769 |

FOREIGN PATENT DOCUMENTS

| | | |
|---|---|---|
| JP | 56-125022 A | 10/1981 |
| JP | 5-305049 | 11/1993 |
| JP | 05305049 | 11/1993 |
| JP | 9-66014 | 3/1997 |
| JP | 9-135798 | 5/1997 |
| JP | 9-164101 | 6/1997 |
| JP | 10-75924 A | 3/1998 |
| JP | 11-99088 | 4/1999 |
| JP | 11-267079 | 5/1999 |
| JP | 11-235301 | 8/1999 |
| JP | 2000-102492 | 4/2000 |
| JP | 2002-326944 | 11/2002 |

(Continued)

OTHER PUBLICATIONS

English Machine Translation of JP 2003-055122.*

(Continued)

*Primary Examiner*—Jennifer A Chriss
(74) *Attorney, Agent, or Firm*—Lowe Hauptman Ham & Berner LLP

(57) ABSTRACT

An indoor cleaning tool having a dry fibrous base material is provided. An antigenicity-reducing composition including an antigenicity-reducing component, an oil and a surfactant are applied to the fibrous base material. Preferably, the antigenicity-reducing component is an extract of an *olea* or a *ligustrum* plant extracted with water or an organic solvent.

28 Claims, 5 Drawing Sheets

FOREIGN PATENT DOCUMENTS

Figure 1:
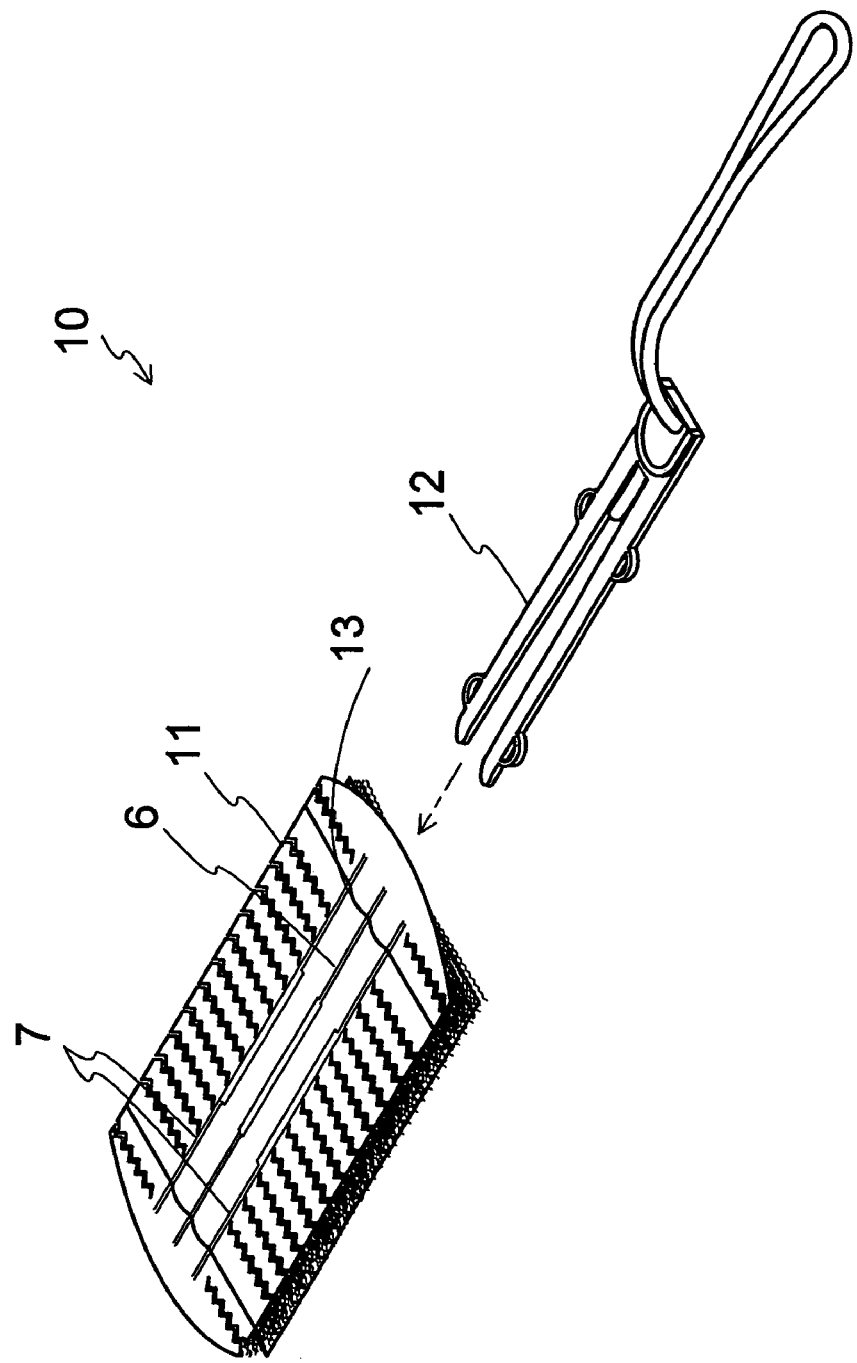

| | | |
|---|---|---|
| JP | 2002-369783 | 12/2002 |
| JP | 2003-55122 | 2/2003 |
| JP | 2003055122 | 2/2003 |
| JP | 2003-79554 | 3/2003 |
| JP | 2003-261899 | 9/2003 |
| JP | 2003-265389 | 9/2003 |
| JP | 2003-334240 | 11/2003 |
| JP | 2003334240 | 11/2003 |
| JP | 2004-65731 | 3/2004 |
| JP | 2004-81840 | 3/2004 |
| JP | 2004065731 | 3/2004 |

OTHER PUBLICATIONS

European Search Report dated Apr. 6, 2006, for Application No. EP 05 25 7506.

* cited by examiner

CLEANING TOOL

This application is based on and claims the benefit of priority from Japanese Patent Application No. 2004-381391, filed on 28 Dec. 2004, the content of which is incorporated herein by reference.

BACKGROUND OF THE INVENTION

The present invention relates to an indoor cleaning tool equipped with a fibrous base material, more specifically, to a cleaning tool that can reduce the antigenicity of allergy inducing substances.

RELATED ART

In recent years, there has been a steady increase in the number of people afflicted with allergic diseases such as allergic rhinitis and bronchial asthma. The substances that provoke these allergic diseases are referred to as allergens, of which already approximately 200 types have been identified to date. Mites, mite carcasses, pet hair, and pollen are typical examples thereof. These allergens can provoke various allergic symptoms through contact with or entry into the body.

In these cases, using chemicals or the like to kill the mites and the like that provoke allergies does not provide a complete solution since the mite carcasses also have antigenicity. Thus, the alleviation of allergic symptoms or the prevention of a new sensitization to allergens requires either a complete removal of allergens from the living space or a reduction of the antigenicity of allergy inducing substances by denaturing allergens thereof.

In Japanese Patent Application Laid-open Publication No. 2003-55122 (hereinafter Patent Document 1), as an agent for reducing antigenicity of allergy inducing substances described above, allergen-inactivating agents prepared from at least one plant selected from the Oleaceae, for example, *Olea europaea* or *Ligustrum obtusifolium*, have been disclosed.

In Japanese Patent Application Laid-open Publication No. 2003-334240 (hereinafter Patent Document 2), also, as the agents that can be sprayed or applied in an aqueous state onto tatami floor mats, carpets and floors, allergen-reducing agents including an aqueous solution containing aluminum sulfate and sodium sulfate as the active components have been disclosed.

Furthermore, in Japanese Patent Application Laid-open Publication No. H5-305049 (hereinafter Patent Document 3), as the cleaning tools for removing indoor dust and dirt using static electricity, there have also been disclosed cleaning tools for adsorbing and collecting indoor dust and dirt using non-woven fabric constituted of olefinic extra-fine fibers formed into an electret to store static electricity therein. In Japanese Patent Application Laid-open Publication No. 2004-65731 (hereinafter Patent Document 4) cleaning cloths that have a high capacity to adsorb and collect indoor dust and dirt, which is elevating charge generated upon cleaning (wiping), by combining fibrous materials of different triboelectric series have been also disclosed.

In cleaning tools such as dusters, mops and wipers used to remove indoor dust and dirt, allergens adhere to the cleaning tool during cleaning and remain thereon as they are for a long period. As described above, for the alleviation of allergic symptoms or for the prevention of a new sensitization to allergens, the reduction of the antigenicity of allergens held on the cleaning tool would also be required.

However, the agents of the above-described Patent Documents 1 and 2 are for use of spraying or applying them directly to places which can be in contact with the body, such as on tatami floor mats, carpets, floors and clothes. This makes it necessary to wipe away the agent or to remove it with a vacuum cleaner after application, resulting in a burden on the user. However, no easy method has been researched for eliminating allergy inducing substances on floors and furniture which are cleaned most frequently. Also, in the conventional methods, the object to be cleaned becomes wet, and therefore it requires time to dry it. Furthermore, no research has been done on reducing antigenicity of allergy inducing substances contained in dust and dirt collected on the cleaning tools such as mops having fibrous base materials.

In particular, as the indoor cleaning tools, dry tools equipped with disposable and replaceable fibrous base materials in sheet or brush form which contain essentially no moisture have been well-received in the market. For such cleaning tools, it is required to be capable of adsorbing and collecting dirt and dust leaving no wiping mark on the object to be cleaned, and adsorb the antigenicity-reducing component to the surface of the fibrous base material or impregnate that surface with the component.

With regard to this, in Patent Documents 3 and 4, no research has been performed on the cleaning tool considering the compatibility between the above-described capability of collecting dirt and dust, of the prevention from leaving the wiping mark on the object to be cleaned, and capability of both adsorption and the impregnation of the antigenicity-reducing component.

SUMMARY OF THE INVENTION

The present invention has been made in view of the above-described problems, aiming at providing a cleaning tool capable of adsorbing and collecting dust or dirt without leaving the wiping mark on the object to be cleaned, and further reducing the antigenicity of allergy inducing substance adhering to the cleaning tool.

The present inventors have diligently researched to solve the above-described problems and have discovered that the problems can be solved by using fibers having electrostatic charge properties for the fibrous base material of the cleaning tool and by applying an antigenicity-reducing component to the fibrous base material, thus achieving the present invention. More specifically, the present invention provides the following.

A first aspect of the present invention is a cleaning tool for indoor wiping including: an electrostatic fibrous base material charged electrostatically at least during use; in which the electrostatic fibrous base material has an antigenicity-reducing component which reduces antigenicity of allergy-inducing matter.

The cleaning tool according to the invention is equipped with a dry fibrous base material with an electrostatic charge property so as to be capable of collecting dirt and dust without leaving any wiping marks. Accordingly, this cleaning tool can be used for such objects as TV sets and glassware on which consumers desire that no wiping marks remain. Furthermore, since an antigenicity-reducing component is applied to the cleaning tool, allergy inducing substances which have adhered to the cleaning tool can be reduced. Moreover, the antigenicity-reducing components can be easily applied to the fibrous base material, and when respective components are applied in limited quantities, it is possible to prevent the transition of the antigenicity-reducing components from the fibrous base material side to the object side to be cleaned while using the cleaning tool.

A second aspect of the present invention is a cleaning tool as in the first aspect of the present invention in which the fibrous material is a fiber processed with electret treatment.

In this embodiment, since a charge by electret-forming treatment is utilized, the charge can be maintained semi-permanently requiring no friction of the cleaning tool with an object to be cleaned. In this invention, "electret treatment" means making base material electrically charged and polarized semi-permanently. Accordingly, the cleaning tool can always adsorb and collect dirt and dust so as to be capable of reducing the antigenicity of allergy inducing substances in removing the dirt and dust without leaving wiping marks. Furthermore, since the electrical charge is not transferred to the allergy inducing substance, it hardly falls away so as to be easily captured on the cleaning tool. Therefore, even the cleaning tool which has adsorbed and collected allergy inducing substances but is still usable can be safely kept in house.

A third aspect of the present invention is a cleaning tool as in the first aspect of the present invention in which the electrostatic fibrous base material is a combination of two or more types of fiber having different triboelectric series.

In this embodiment, because of the combination of fibers of different triboelectric series, static electricity can be easily generated by the friction among fibers such that no friction is required between an object to be cleaned. Furthermore, even dirt and dust charged either positively or negatively can be adsorbed and collected to the fibers so as to enable the efficient absorption of allergy inducing substances A fourth aspect of the present invention is a cleaning tool as in the first to third aspects of the present invention in which a fibrous material constituting the electrostatic fibrous base material is hydrophobic.

According to this embodiment, since fiber composition is hydrophobic, the charge state thereof can be maintained for a long period of time.

A fifth aspect of the present invention is a cleaning tool as in the first to fourth aspects of the present invention in which the antigenicity-reducing component is provided in a state of a solution into which the antigenicity-reducing component is dissolved.

According to this embodiment, the antigenicity-reducing component is applied as diluents diluted in water or ethanol to the fibrous base material such that it can be applied uniformly to the fibers. Accordingly, a reaction when the antigenicity-reducing component is contacted with the allergy inducing substances contained in the wiped-off dirt and dust can be efficiently carried out. In this case, it is possible to supplement a dilute solution with surfactants allowing to easily stick to the fibers and binder components such as organic macromolecular substances allowing to be readily fixed to the fibers.

A sixth aspect of the present invention is a cleaning tool as in the first to fifth aspects of the present invention in which the antigenicity-reducing component is a plant extract component.

According to this embodiment, the antigenicity-reducing component to be used is of a plant origin so as to be highly physiologically safe to the human body.

A seventh aspect of the present invention is a cleaning tool as in the first to sixth aspects of the present invention in which the antigenicity-reducing component is an extract from an olea or ligustrum plant extracted by using water or an organic solvent.

According to this embodiment, extracts of *olea* or *ligustrum* plants in water or in an organic solvent (hereinafter referred to as olive extracts) are so excellent in the antigenicity-reducing activity that they can reduce the antigenicity even by the application of smaller amounts thereof. Also, some types of conventional plant-derived antigenicity-reducing components per se have color, thus it causes such problems as coloring of the fibrous base material when applied thereto. However, since the olive extract itself is yellow to yellowish brown in color, it becomes almost transparent when diluted and applied to the fibrous base material, and thus this enables preventing coloring of the base materials.

An eighth aspect of the present invention is a cleaning tool as in the first to seventh aspects of the present invention in which the antigenicity-reducing component is oleuropein.

Oleuropein used in this embodiment is a phenolic iridoid glycoside contained in the above-described Oleaceae plants (such as *Olea europaea* or *Ligustrum obtusifolium*) in large quantities. This Iridoid glycoside has a formyl group and a hydroxyl group, which are thought to exert the antigenicity-reducing action through the binding thereof with an amino group contained in the allergen protein.

A ninth aspect of the present invention is a cleaning tool as in the seventh or eighth aspects of the present invention in which the electrostatic fibrous base material is white.

According to this embodiment, since the olive extract and oleuropein described above have little coloring, there is no problem with the fibrous base material being colored. As a result, since white fibrous base materials can be used similarly as before, dust and dirt adhering to the base materials can be easily seen.

A tenth aspect of the present invention is a cleaning tool as in the first to ninth aspects of the present invention in which the antigenicity-reducing component is provided 0.001 percent or more by weight and 10 percent or less by weight per 100 percent weight portion of the electrostatic fibrous material.

According to this embodiment, an adequate antigenicity-reducing effect can be obtained by applying the antigenicity-reducing component in such a very small amount as no less than 0.001 percent by weight relative to the entire fibrous base material. Furthermore, when the amount of the antigenicity-reducing component exceeds 10 percent by weight, the stability over time thereof becomes poor.

EFFECTS OF THE INVENTION

According to the present invention, a cleaning tool can be provided which is capable of reducing the antigenicity of allergy inducing substances adhering to the cleaning tool and leaving no wiping marks on the object to be cleaned after wiping off dirt and dust therefrom.

BRIEF DESCRIPTION OF THE DRAWINGS

FIG. 1 shows a perspective drawing showing an example of a cleaning tool according to the present invention.

FIG. 2 shows an exploded perspective drawing of the fibrous base material in FIG. 1.

FIG. 3 shows an exploded perspective drawing of the fibrous base material according to the second embodiment of the present invention.

FIG. 4 shows a perspective drawing showing another example of a cleaning tool according to the present invention.

Figure 5:
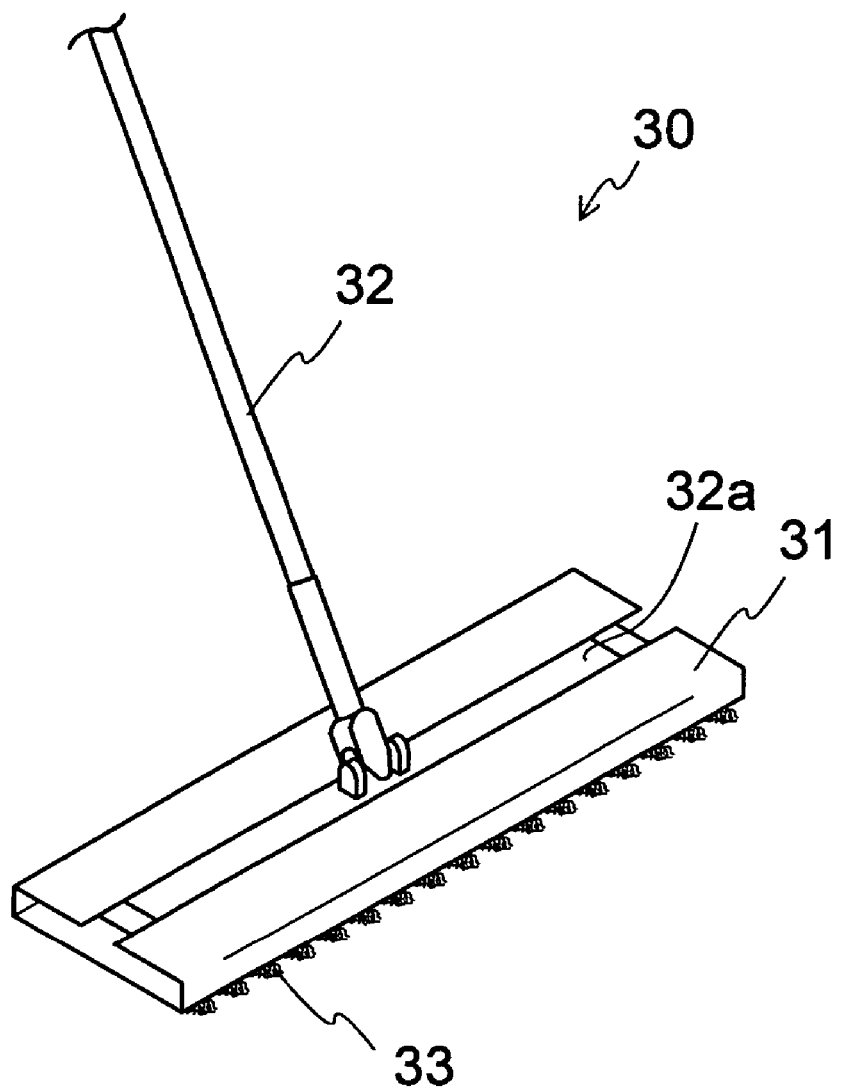

FIG. 5 shows a perspective drawing showing yet another example of a cleaning tool according to the present invention.

DETAILED DESCRIPTION OF THE INVENTION

In the following, the best mode for carrying out the present invention will be explained.

Antigenicity-Reducing Component

The "antigenicity-reducing component" used in the present invention reduces the antigenicity of allergy inducing substance to suppress allergic symptoms, preferably being the component of a plant-origin. Herein, the allergy inducing substance (allergen) includes inhaled allergens such as mites, house dust, animal, fungi and insects, in addition to cedar pollen and oryza pollen.

Such antigenicity-reducing components are not particularly limited, including the above-described olive extracts, privet extracts, and extracts of pomegranate, neem, persimmon, tea, bamboo, perilla, peppermint, Japanese Hinoki cypress (*Chamaecyparis obtusa*), Hiba arborvitae (*Thujopsis dolabrata*), eucalyptus, tea tree, etc. Examples of extracted compounds include tannic acid, gallic acid, etc. Other examples include: high-molecular compounds having a side chain of linear macromolecular repeating units including monovalent or higher phenol groups such as poly (para-vinyl phenol); high-molecular compounds having monovalent phenol groups such as dioxybenzoic acid polymer as the repeating unit, bivalent or higher benzene sulfonates having a polyoxyethylene chain and/or an ethylene chain such as disodium lauryl diphenyl ether disulfonate in its molecule; and/or bivalent or higher sulfates having a polyoxyethylene chain and/or an ethylene chain in its molecule; and/or bivalent or higher hydrosulfate having polyoxyethylene chain and/or ethylene chain in its molecule, alcohols having a terpenoid skeleton; hydroxy benzoates such as 2,5-dihydroxy benzoic acid; aromatic hydroxy compounds; carbonates of alkaline metals; alum; lauryl benzene sulfonates; lauryl sulfates; polyoxyethylene lauryl ether sulfates; phosphates; zinc sulfate and/or lead acetate; etc.

Of the components described above, the antigenicity-reducing component preferably includes an olive extract. The "olive extract" in the present invention includes extracts of the olea or ligustrum plants in water or an organic solvent. Also, the antigenicity-reducing component is preferably oleuropein. Oleuropein is an iridoid glycoside having a formyl group and a hydroxyl group. These groups are thought to bind with the amino groups contained in the allergen protein so as to reduce the antigenicity thereof. Specifically, the olive extract as described in Patent Document 1 above can be used.

Also, tannic acid is thought to reduce antigenicity by binding the hydroxyl groups in polyphenol bonding thereof with the amino group and the peptide section of the allergen protein.

The antigenicity-reducing component described above may be applied usually in a state of a solution containing an active ingredient such as oleuropein and an extract thereof (hereinafter referred to as antigenicity-reducing agent). The olive extract described above is an example of an antigenicity-reducing agent, which can be used as a solution containing ethanol and water besides oleuropein.

Various ingredients other than the above-described antigenicity-reducing components can also be applied to the cleaning tool of the present invention as long as they do not significantly alter the characteristics of the cleaning tool. Such ingredients may be applied to the cleaning tool either mixed together with or applied separately from the antigenicity-reducing agent. For example, a supplement may be added to the antigenicity-reducing agent to enhance the reactivity thereof. Examples of the supplement are hygroscopic compositions including alkaline earth metal salts, etc. Further, lubricants, surfactants and like may be added to facilitate the adhesion of the antigenicity-reducing agent to the fibrous base materials.

Cleaning Tool

First Embodiment

Static Electricity-Generating Type

Next, a cleaning tool to which is applied the above-described antigenicity-reducing component will be explained. The static electricity-generating type cleaning tool is an indoor cleaning tool equipped with a substantially moisture-free fibrous base material, and it is not particularly limited so long as the cleaning tool generates static electricity by friction between fibrous base material and a wiped surface, and friction among fibers.

As the fibers used in the cleaning tool, any fibers which have been conventionally used in the non-woven fabric and clothing can be used, but they are preferably synthetic fibers. As the synthetic fibers, those of polyethylene terephthalate, polyethylene, polypropylene, polyvinyl chloride, polytetrafluoroethylene, polystyrene, nylon and such can be used. As the natural fibers, wool and such can be used.

Furthermore, a combination of the above-described fibers can be used. When fibers are combined for use, both fibers having a charge property showing minus-polarity and fibers having a charge property showing positive polarity are alternately arranged. Thus, using fibers with opposite polarities alternately, dust and dirt can be adsorbed and collected without relying on the polarity thereof. Furthermore, static electricity can be efficiently generated by frictions among fibers themselves even without frictions between fibers and the wiped surface of an object.

In this case, for efficiently generating/maintaining static electricity, it is preferable to make fibers as hydrophobic as possible.

As the non-woven fabric, spun-bonded non-woven fabric, melt-blown non-woven fabric and spun-laced non-woven fabric are preferably used.

Examples of Cleaning Tools

Figure 2:
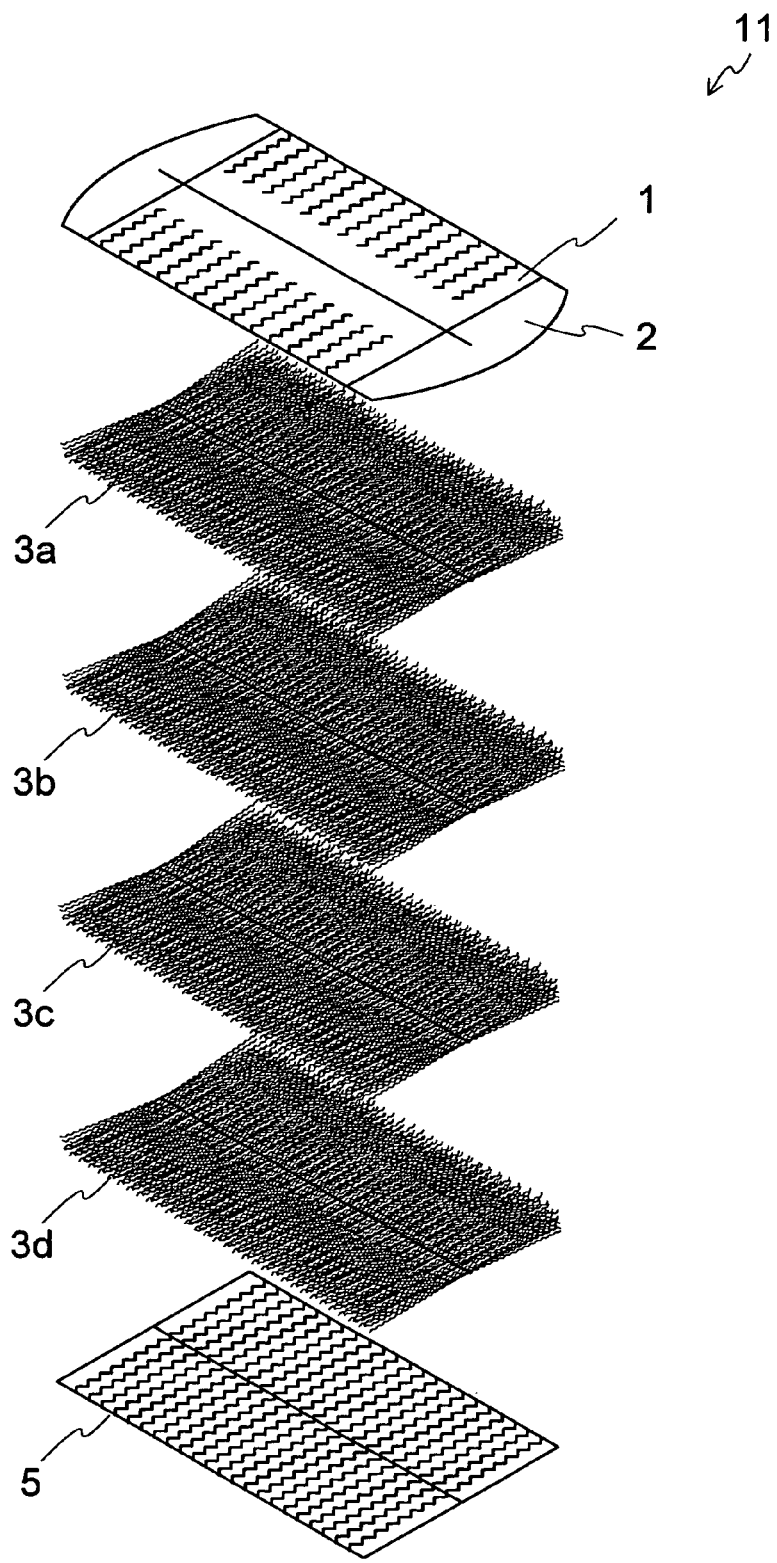
Figure 4:
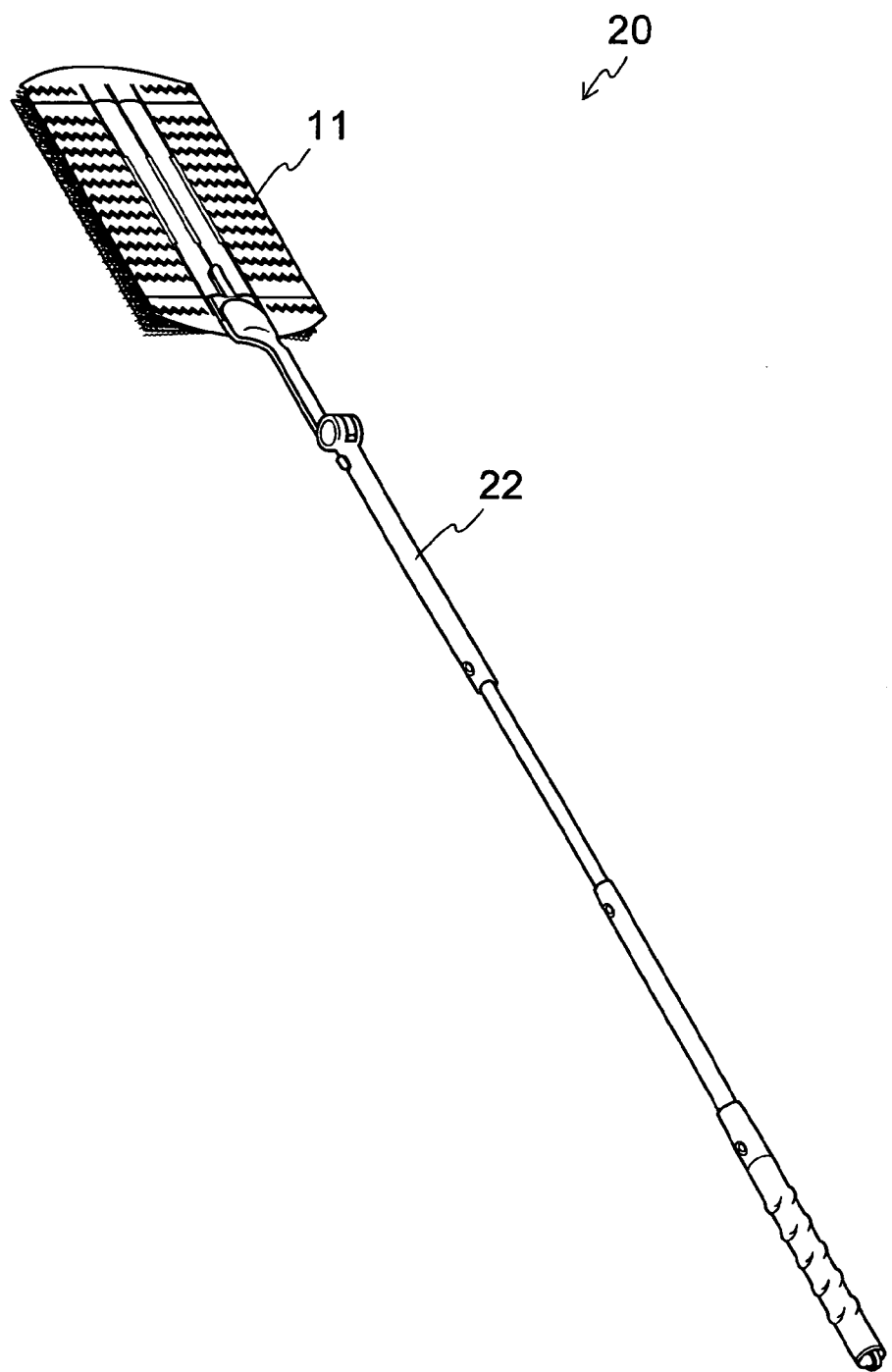

FIGS. 1 and 2 show an example of a cleaning tool. FIG. 1 is a perspective view of the cleaning tool, while FIG. 2 is an exploded perspective view of the cleaning sheet from in FIG. 1. As shown in FIG. 1, this cleaning tool 10 is of a so-called "handy-type," including a cleaning sheet 11 corresponding to the fibrous base material of the present invention and a handle 12. The handle 12 is appropriately interchangeable. For example, a handle 22 as shown in FIG. 4 can be mounted to allow the cleaning tool in FIG. 1 to be used for cleaning high places or narrow places that are difficult to reach.

As shown in FIG. 2, the cleaning sheet 11 is formed from the following layers, starting in sequence from top to bottom: a protective sheet 1 formed from non-woven fabric cut into multiple strips; a base sheet 2 also formed from non-woven fabric cut into multiple strips; a first fiber bundle 3*a* formed from fiber tow; a second fiber bundle 3*b* formed from fiber tow; a third fiber bundle 3*c* formed from fiber tow; a fourth fiber bundle 3*d* formed from fiber tow; and a strip sheet 5 in which multiple strips are formed. In this embodiment, the first fiber bundle 3*a*, the second fiber bundle 3*b*, the third fiber bundle 3c and the fourth fiber bundle 3d constitute the brush section of the present invention. Thus, this brush section provides more effective cleaning. Since the antigenicity-reducing component need only be applied to this brush section, it can be applied more efficiently. Herein, the "brush section" is a section that performs the primary cleaning function in the cleaning tool according to the present invention, may be referred to either a portion or a whole of the fibrous base material. Of the respective layers, the protective sheet 1, the base material sheet 2, the first fiber bundle 3a, the second fiber bundle 3b, the third fiber bundle 3c, the fourth fiber bundle 3d and the strip sheet 5 are all bonded together at the uni-layer-bonding line 6. At the bonding lines 7, only the protective sheet 1, the base material sheet 2, the first fiber bundle 3a and the second fiber bundle 3b are bonded. As a result, a holding space 13 is formed between the protective sheet 1 and the base material sheet 2, allowing the handle 12 to be inserted and fixed. In such "handy-type" cleaning tools 10 and 20, the antigenicity-reducing component is preferably applied only to the brush section including the first fiber bundle 3a, the second fiber bundle 3b, the third fiber bundle 3c and the fourth fiber bundle 3d.

Another Example of a Cleaning Tool

FIG. 5 shows another example of a cleaning tool in the form of a floor-type cleaning tool 30 suitable for cleaning floors. As shown in FIG. 5, in this cleaning tool 30, a cleaning sheet 31 corresponding to the fibrous base material of the present invention is wrapped around a panel at an end 32a of a handle 32 for use. Projections 33 made from tows are formed on the front and back of the cleaning sheet 31, facilitating the cleaning places, such as grooves, that would be difficult to clean with a flat tool. By simply placing the cleaning tool 30 in contact with a floor or the like, the cleaning sheet 31 is able to collect dust and like by the static electricity force. In such a "floor-type" cleaning tool 30, it would be preferable to apply the antigenicity-reducing component to the entire cleaning sheet 31.

Method for Applying Antigenicity-Reducing Component

Methods for applying the antigenicity-reducing component to the cleaning tool described above include the method of spraying or roller-coating the antigenicity-reducing component onto the fibrous base material, the immersion method and the like, but are not restricted to them. Furthermore, when the antigenicity-reducing component is applied, it may be applied as a dilute solution in water or in an organic solvent because an amount of the antigenicity-reducing component to be applied is extremely small. In this case, the solvent of the dilute solution of the antigenicity-reducing component evaporates after the application thereof, resulting in a manufacturing of a cleaning tool applied with the antigenicity-reducing component.

The antigenicity-reducing component is applied in an amount of preferably no less than 0.001 percent by weight and no more than 10 percent by weight, more preferably no less than 0.002 percent by weight and no more than 1 percent by weight, relative to the entire fibrous base material.

When the antigenicity-reducing component is less than 0.001 percent by weight, the antigenicity-reducing rate against the collected dust becomes undesirably insufficient, while, when the antigenicity-reducing component exceeds 10 percent by weight, it becomes undesirably poor in stability over time thereof and also costly.

Second Embodiment

Electret-Forming Treated Type

Figure 3:
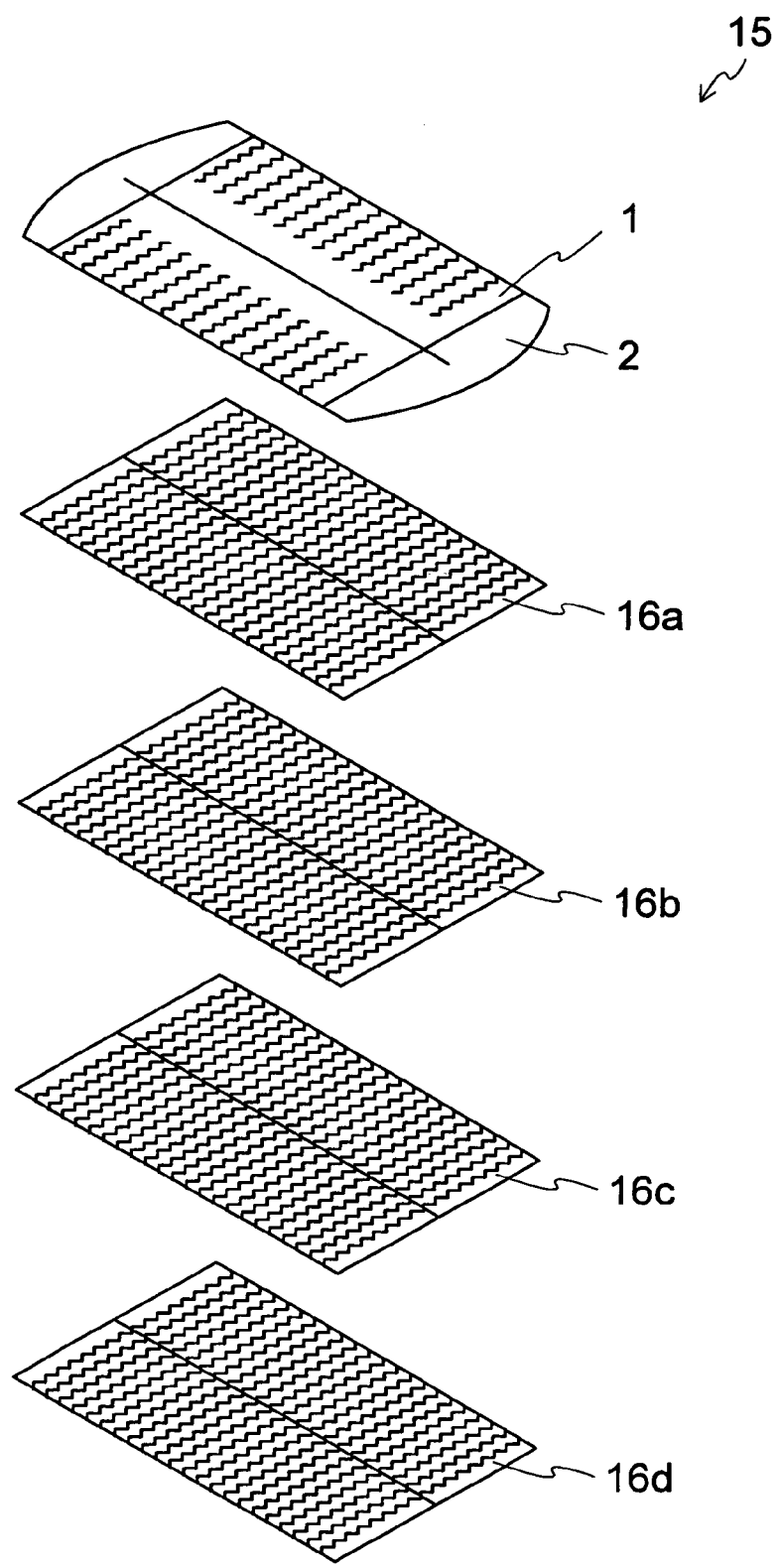

An electret-forming treated type cleaning tool is manufactured by using the fibrous base material formed from the laminated non-woven fabrics cut into strips and making that base material into an "electret", which makes a base material electrically charged and polarized semi-permanently. FIG. 3 shows an exploded perspective view of a cleaning sheet according to a second embodiment of this invention. As shown in FIG. 3, a cleaning sheet 15 is formed from the following layers, starting in sequence from top to bottom: a protective sheet 1 formed from non-woven fabric cut into multiple strips; a base sheet 2 also formed from non-woven fabric cut into multiple strips; a first fiber bundle 16a also formed from non-woven fabric cut into multiple strips; a second fiber bundle 16b; a third fiber bundle 16c; and a fourth fiber bundle 16d.

Fibers used in non-woven fabrics are preferably those of olefins, most suitably polypropylene in particular. The fiber diameter is preferably that of an extra-fine type, not less than 0.1 μm and not more than 10 μm.

Non-woven fabrics are preferably melt-blown non-woven fabric and spun-bonded non-woven fabric, and the specific weight per unit area thereof is preferably not less than 10 g/m$^2$ and not more than 100 g/m$^2$ Electret-forming treatment, which means making a base material electrically charged and polarized semi-permanently, can be performed on fibers in the long fibrous state, non-woven fabrics and cleaning tools after the manufacture thereof by a conventional method known in the art. Methods for applying the electric charge include a method for polarizing a sample with the direct current high voltage, the method for ionizing the atmosphere by applying the direct current high voltage to a needle electrode and applying ions to fibers, and the method for charging fibers by a positive discharge.

Examples

In the following, the present invention will be explained in further detail with reference to examples and comparative examples, but it is not restricted to these examples described below.

Preparation of Antigenicity-Reducing Agent Containing Antigenicity-Reducing Component Olive Extract After the leaves of the olive plant were extracted with water based on the third composition embodiment in Patent Document 1 (20 g of fresh olive leaves placed in 100 g of water, disintegrated in a mixer, then filtered using a filter paper to obtain a filtrate), ethanol was added to prepare a 0.6% oleuropein solution.

Tannic acid (from Wako Pure Chemical Industries, Ltd.) was dissolved in water and ethanol so as to prepare a 15% tannic acid solution.

Preparation of Antigenicity-Reducing Component Dilute Solution

The two types of antigenicity-reducing agents described above were mixed and stirred in the proportions shown in Table 1 to prepare the preparation samples 1-3 of the antigenicity-reducing component dilute solutions. The preparation sample 4 is a case when only water was used as a control

TABLE 1

Combined amount of antigenicity-reducing component in dilute solution (unit: % by weight)

| Name | Sample | Antigenicity-reducing component | Water |
|---|---|---|---|
| Solution added with no antigenicity-reducing component | Preparation sample 4 | — | 100 |
| Tannic acid composition | Preparation sample 1 | 1 | 99 |
|  | Preparation sample 2 | 10 | 90 |
| Oleuropein composition | Preparation sample 3 | 100 | 90 |

Application of Antigenicity-Reducing Component to Cleaning Tool

Next, the above-described preparation samples 1 through 3 of the antigenicity-reducing component dilute solution and the preparation sample 4 (a solution (water) added with no antigenicity-reducing component) were sprayed onto the cleaning tool shown in FIG. 1 (hereinafter referred to as the "handy-type"), and onto the cleaning tool shown in FIG. 4 (hereinafter referred to as the "floor-type"). These cleaning tools used herein were of a static electricity-generating type. First, 3 of fiber tows including the polyethylene/polypropylene side-by-side fibers and a single fiber tow including the nylon fiber were piled to prepare the fiber bundles (3a, 3b, 3c and 3d in FIG. 2). These fiber bundles and the non-woven fabric (the strip sheet 5 in FIG. 2) were bonded together to manufacture the cleaning tool. For each of the floor-type and handy-type, cleaning tools of Examples 1 through 3 (applied with the preparation samples 1 through 3) and that of a first comparative example (applied with the preparation sample 4) were obtained.

For the handy-type tools, the antigenicity-reducing component dilute solution was applied so as to become 5 percent by weight thereof relative to the entire fibrous base material (the sheet 11 in FIG. 1). For the floor-type tools, the aforementioned dilute solution was applied so as to become 7.5 percent by weight thereof relative to the entire fibrous base material (the sheet 31 in FIG. 5).

Evaluation

Evaluation 1: Evaluation of Antigenicity-Reducing Performance

Cleaning tools according to Examples 1, 2 and 3 as well as the comparative example 1 were evaluated for the antigenicity-reducing performance on cedar pollen and dust mites (*Dermatophagoides*) using the procedure described below. The results are shown in Tables 2 and 3. The "reduction rates" in the Tables are the values determined as "100-100×(ELISA allergen amount from a cleaning tool applied with antigenicity-reducing agent)/(ELISA allergen amount from a cleaning tool applied with no antigenicity-reducing agent). The symbols in the tables indicate the following reduction rates:

gr: good reduction rate (50% or more)
  ir: inferior reduction rate (10-50%)
  br: bad reduction rate (0-10%)

Handy-type: Dust containing approximately 0.05 g of mite allergens (*Dermatophagoides*) and approximately 0.01 g of cedar pollen were placed in a glass bottle having a diameter of 9 cm and a height of 17 cm, respectively, and, after the bottle was capped, the dust and cedar pollen were dispersed throughout the internal wall of the bottle, respectively. The top was removed and the handy-type cleaning tool was used to wipe away the dust and cedar pollen, respectively. The allergens were extracted from this cleaning tool with an extraction fluid, and quantified using the ELISA method.

Floor-type: Dust containing approximately 0.05 g of mite allergens (*Dermatophagoides*), and approximately 0.01 g of cedar pollen were dispersed on a floor panel approximately 30 cm×30 cm, respectively, and wiped away with the floor-type cleaning tool. The allergens were extracted from this cleaning tool with an extraction fluid and quantified using the ELISA method, respectively.

In this case, a phosphate buffer (pH 7) was used as the extraction fluid. The ELISA (enzyme-linked immunosorbent assay) method is a type of EIA (enzyme immunoassay) to quantify a substance (antigen or antibody) utilizing a color development by an enzyme linked to antigen or antibody taking place in antigen-antibody reactions. In this case, the ELISA method is a sandwich method in which a substance to be detected (allergen) is quantified by sequentially using two types of antibodies as if sandwiching the antigen.

TABLE 2

Cedar pollen antigenicity reduction rate

|  | Reduction rate | |
|---|---|---|
| Test sample | Handy-type | Floor-type |
| Comparative example 1 | br | br |
| Example 1 | ir | ir |
| Example 2 | gr | gr |
| Example 3 | gr | gr |

TABLE 3

Mite antigenicity reduction rate

|  | Reduction rate | |
|---|---|---|
| Test sample | Handy-type | Floor-type |
| Comparative example 1 | br | br |
| Example 1 | br | ir |
| Example 2 | gr | gr |
| Example 3 | gr | gr |

From the results in Tables 2 and 3, it was confirmed that the floor-type cleaning tool showed the antigenicity-reducing effect with either one of the antigenicity-reducing components. In the handy-type cleaning tool of Example 1, however, the antigenicity-reducing component was applied in smaller amounts such that the effect was insufficient.

Evaluation 2: Evaluation of Antigenicity Reducing Effect after Heating and Light Irradiation Heating test: For the cleaning tools in Examples 2 and 3, the only fibrous base material was placed in a paper container and packaged in the case of the handy-type cleaning tools, and packaged with film in a pillow-shape in the case of the floor-type cleaning tool. The packages were left standing indoors away from direct light in thermostatic chambers at 40 and at 50, respectively. Right after the initiation of the test, and after one month, allergens were measured using the same method as in the Evaluation 1.

Light irradiation test: Fibrous base materials from both the handy-type and floor-type cleaning tools were not packaged, and were left standing as the sheets themselves under a xenon lamp weather meter for the equivalent of one month and six months under sunlight. Allergens were measured using the same method as in the Evaluation 1.

Results are shown in Table 4, with the reduction rates and symbols in the table indicating the same things as in Tables 2 and 3. For both the cleaning tools of Examples 2 and 3, the reduction effect was maintained after exposure to heat for one month. The reduction effect was also maintained after exposure to the light irradiation.

TABLE 4

| | | Mite antigenicity reduction rate | | | |
| --- | --- | --- | --- | --- | --- |
| | | Example 2 | | Example 3 | |
| Condition | Elapsed time | Handy-type | Floor-type | Handy-type | Floor-type |
| Immediately after application | 0 days | gr | gr | gr | gr |
| Room Temperature | One month | gr | gr | gr | gr |
| 40 | One month | gr | gr | gr | gr |
| 50 | One month | gr | gr | gr | gr |
| Light irradiation | One month equivalent | gr | gr | gr | gr |
| Light irradiation | Six months equivalent | gr | — | gr | — |

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

INDUSTRIAL APPLICABILITY

The present invention can be preferably used as an indoor cleaning tool equipped with fibrous base materials.

What is claimed is:

1. A cleaning tool for indoor wiping comprising:
an electrostatic fibrous base material electrostatically chargeable at least during use;
wherein
the electrostatic fibrous base material comprises a combination of two or more types of fiber having different triboelectric series and an antigenicity-reducing component for reducing antigenicity of allergy-inducing substances, and
the antigenicity-reducing component includes oleuropein derived from an olive leaf extract and is achieved by
adding ethanol to the extract to prepare a 0.6% oleuropein solution defining an antigenicity-reducing agent;
adding at least water to the antigenicity-reducing agent to prepare an antigenicity-reducing component dilute solution; and
applying the antigenicity-reducing component dilute solution to the fibrous base material to obtain the antigenicity-reducing component.

2. The cleaning tool according to claim 1, wherein the electrostatic fibrous base material comprises fibers processed with electret treatment.

3. The cleaning tool according to claim 1, wherein the electrostatic fibrous base material is hydrophobic.

4. The cleaning tool according to claim 1, further comprising at least one of a binder component and a surfactant added to the antigenicity-reducing component dilute solution.

5. The cleaning tool according to claim 1, wherein the electrostatic fibrous base material is white.

6. The cleaning tool according to claim 1, wherein the antigenicity-reducing component is provided at 0.001 percent or more by weight and 10 percent or less by weight per 100 percent weight portion of the electrostatic fibrous base material.

7. The cleaning tool according to claim 1, wherein the antigenicity-reducing agent further comprises a hygroscopic supplement.

8. The cleaning tool according to claim 1, wherein the combination has fibers of a first type having a charge property showing minus-polarity and another fibers of a second type having a charge property showing positive polarity, wherein the fibers of said first and second type are alternately arranged.

9. A cleaning tool as defined in claim 1, further comprising:
a cleaning sheet comprising the electrostatic fibrous base material; and
a handle mounted to the cleaning sheet.

10. The cleaning tool according to claim 9, wherein the cleaning sheet further comprises:
a protective sheet attached on the electrostatic fibrous base material and both sheets are made from non-woven fabric transversely cut into multiple strips;
a strip sheet located on a bottom of the cleaning sheet; and
a brush section, including at least one fiber bundle, with the antigenicity-reducing component provided between the protective sheet and the strip sheet.

11. The cleaning tool according to claim 10, wherein the brush section comprises a first fiber bundle attached to a bottom of the base material sheet and a second fiber bundle in contact with a bottom of the first fiber bundle.

12. The cleaning tool according to claim 11, wherein the protective sheet, the base material sheet, the first and second fiber bundles, the brush section and the strip sheet are bonded together along a first bonding line.

13. The cleaning tool according to claim 12, wherein
the cleaning sheet further comprises at least one second bonding line extending along a longitudinal direction of the cleaning sheet to bond the protective sheet, the base material sheet, the first and second fiber bundles together; and
the brush section and the strip sheet are not bonded to the protective sheet, the base material sheet, the first and second fiber bundles along said second bonding line.

14. The cleaning tool according to claim 13, wherein the cleaning sheet further comprises a holding space configured between the protective sheet and the base material sheet and between the first and second bonding lines to allow the handle to be inserted and fixed in the cleaning sheet.

15. The cleaning tool according to claim 10, wherein each said fiber bundle is made from non-woven fabric transversely cut into multiple strips.

16. The cleaning tool according to claim 9, wherein said combination has fibers of a first type having a charge property showing minus-polarity and another fibers of a second type having a charge property showing positive polarity, and the fibers of said first and second type are alternately arranged.

17. The cleaning tool according to claim 1, wherein the antigenicity-reducing component dilute solution has 10 percent by weight of the antigenicity-reducing agent and 90 percent by weight of water.

18. The cleaning tool according to claim 8, wherein the fibrous base material comprises non-woven fabrics cut into strips, and the fibers of the non-woven fabrics comprise polypropylene and have a fiber diameter not less than 0.1 μm and not more than 10 μm.

19. The cleaning tool according to claim 18, wherein the nonwoven fabric defines fiber bundle layers.

20. A cleaning tool for indoor wiping comprising:

an electrostatic fibrous base material electrostatically chargeable at least during use;

wherein the electrostatic fibrous base material comprises a fiber bundle and an antigenicity-reducing component added to said fibrous base material for reducing antigenicity of allergy-inducing substances, and the antigenicity-reducing component includes oleuropein derived from an olive leaf extract and is achieved by adding ethanol to the extract to prepare a 0.6% oleuropein solution defining an antigenicity-reducing agent;

adding at least water to the antigenicity-reducing agent to prepare an antigenicity-reducing component dilute solution; and applying the antigenicity-reducing component dilute solution to the fibrous base material to obtain the antigenicity-reducing component.

21. The cleaning tool according to claim 20, wherein the fiber bundle is processed with electret treatment.

22. The cleaning tool according to claim 20, wherein the fiber bundle is hydrophobic.

23. The cleaning tool according to claim 20, further comprising at least one of a binder component and a surfactant added to the antigenicity-reducing component dilute solution.

24. The cleaning tool according to claim 20, wherein the electrostatic fibrous base material is white.

25. The cleaning tool according to claim 20, wherein the antigenicity-reducing component is provided at 0.001 percent or more by weight and 10 percent or less by weight per 100 percent weight portion of the electrostatic fibrous base material.

26. The cleaning tool according to claim 20, wherein the antigenicity-reducing component dilute solution has 10 percent by weight of the antigenicity-reducing agent and 90 percent by weight of water.

27. The cleaning tool according to claim 20, wherein the fibrous base material comprises non-woven fabrics cut into strips, and the fiber bundle of the non-woven fabrics comprises polypropylene and has a fiber diameter not less than 0.1 μm and not more than 10 μm.

28. The cleaning tool according to claim 27, wherein the nonwoven fabric defines fiber bundle layers.

* * * * *